(12) United States Patent
Locke et al.

(10) Patent No.: US 12,005,179 B2
(45) Date of Patent: Jun. 11, 2024

(54) PRINTED ABSORBENT FOR USE IN WOUND FLUID COLLECTION CANISTERS

(71) Applicant: Solventum Intellectual Properties Company, Maplewood, MN (US)

(72) Inventors: Christopher B. Locke, Bournemouth (GB); Timothy M. Robinson, Wimbourne (GB)

(73) Assignee: Solventum Intellectual Properties Company, Maplewood, MN (US)

( * ) Notice: Subject to any disclaimer, the term of this patent is extended or adjusted under 35 U.S.C. 154(b) by 242 days.

(21) Appl. No.: 17/424,465

(22) PCT Filed: Feb. 4, 2020

(86) PCT No.: PCT/US2020/016558
§ 371 (c)(1),
(2) Date: Jul. 20, 2021

(87) PCT Pub. No.: WO2020/163313
PCT Pub. Date: Aug. 13, 2020

(65) Prior Publication Data
US 2022/0072218 A1 Mar. 10, 2022

Related U.S. Application Data

(60) Provisional application No. 62/803,031, filed on Feb. 8, 2019.

(51) Int. Cl.
*A61M 1/00* (2006.01)
(52) U.S. Cl.
CPC .............. *A61M 1/882* (2021.05); *A61M 1/60* (2021.05); *A61M 1/98* (2021.05); *A61M 1/982* (2021.05)

(58) Field of Classification Search
CPC ........ A61M 1/882; A61M 1/60; A61M 1/982; A61M 1/98; A61M 1/88
(Continued)

(56) References Cited

U.S. PATENT DOCUMENTS

| 1,355,846 A | 10/1920 | Rannells |
| 2,547,758 A | 4/1951 | Keeling |

(Continued)

FOREIGN PATENT DOCUMENTS

| AU | 550575 B2 | 3/1986 |
| AU | 745271 B2 | 3/2002 |

(Continued)

OTHER PUBLICATIONS

Louis C. Argenta, MD and Michael J. Morykwas, PhD; Vacuum-Assisted Closure: A New Method for Wound Control and Treatment: Clinical Experience; Annals of Plastic Surgery; vol. 38, No. 6, Jun. 1997; pp. 563-576.

(Continued)

*Primary Examiner* — Rafael A Ortiz

(57) ABSTRACT

A canister for a wound therapy includes a canister body and a plurality of superabsorbent projections. The canister body is configured to contain wound exudate collected from a wound side. The plurality of superabsorbent projections are fixed to and extend from at least a portion of an interior surface of the canister, and may be formed in a plurality of shapes or patterns comprising circles, squares, hoops/halos, a range of lines, or any combination of said shapes.

15 Claims, 5 Drawing Sheets

(58) Field of Classification Search
USPC .................................................. 206/204
See application file for complete search history.

(56) References Cited

U.S. PATENT DOCUMENTS

| | | | |
|---|---|---|---|
| 2,632,443 A | 3/1953 | Lesher | |
| 2,682,873 A | 7/1954 | Evans et al. | |
| 2,910,763 A | 11/1959 | Lauterbach | |
| 2,969,057 A | 1/1961 | Simmons | |
| 3,066,672 A | 12/1962 | Crosby, Jr. et al. | |
| 3,367,332 A | 2/1968 | Groves | |
| 3,520,300 A | 7/1970 | Flower, Jr. | |
| 3,568,675 A | 3/1971 | Harvey | |
| 3,648,692 A | 3/1972 | Wheeler | |
| 3,682,180 A | 8/1972 | McFarlane | |
| 3,826,254 A | 7/1974 | Mellor | |
| 4,080,970 A | 3/1978 | Miller | |
| 4,096,853 A | 6/1978 | Weigand | |
| 4,139,004 A | 2/1979 | Gonzalez, Jr. | |
| 4,165,748 A | 8/1979 | Johnson | |
| 4,184,510 A | 1/1980 | Murry et al. | |
| 4,233,969 A | 11/1980 | Lock et al. | |
| 4,245,630 A | 1/1981 | Lloyd et al. | |
| 4,256,109 A | 3/1981 | Nichols | |
| 4,261,363 A | 4/1981 | Russo | |
| 4,275,721 A | 6/1981 | Olson | |
| 4,284,079 A | 8/1981 | Adair | |
| 4,297,995 A | 11/1981 | Golub | |
| 4,333,468 A | 6/1982 | Geist | |
| 4,373,519 A | 2/1983 | Errede et al. | |
| 4,382,441 A | 5/1983 | Svedman | |
| 4,392,853 A | 7/1983 | Muto | |
| 4,392,858 A | 7/1983 | George et al. | |
| 4,419,097 A | 12/1983 | Rowland | |
| 4,465,485 A | 8/1984 | Kashmer et al. | |
| 4,475,909 A | 10/1984 | Eisenberg | |
| 4,480,638 A | 11/1984 | Schmid | |
| 4,525,166 A | 6/1985 | Leclerc | |
| 4,525,374 A | 6/1985 | Vaillancourt | |
| 4,540,412 A | 9/1985 | Van Overloop | |
| 4,543,100 A | 9/1985 | Brodsky | |
| 4,548,202 A | 10/1985 | Duncan | |
| 4,551,139 A | 11/1985 | Plaas et al. | |
| 4,569,348 A | 2/1986 | Hasslinger | |
| 4,605,399 A | 8/1986 | Weston et al. | |
| 4,608,041 A | 8/1986 | Nielsen | |
| 4,640,688 A | 2/1987 | Hauser | |
| 4,655,754 A * | 4/1987 | Richmond | A61M 1/60 |
| | | | 604/323 |
| 4,664,662 A | 5/1987 | Webster | |
| 4,710,165 A | 12/1987 | McNeil et al. | |
| 4,733,659 A | 3/1988 | Edenbaum et al. | |
| 4,743,232 A | 5/1988 | Kruger | |
| 4,758,220 A | 7/1988 | Sundblom et al. | |
| 4,787,888 A | 11/1988 | Fox | |
| 4,826,494 A | 5/1989 | Richmond et al. | |
| 4,838,883 A | 6/1989 | Matsuura | |
| 4,840,187 A | 6/1989 | Brazier | |
| 4,863,449 A | 9/1989 | Therriault et al. | |
| 4,872,450 A | 10/1989 | Austad | |
| 4,878,901 A | 11/1989 | Sachse | |
| 4,897,081 A | 1/1990 | Poirier et al. | |
| 4,906,233 A | 3/1990 | Moriuchi et al. | |
| 4,906,240 A | 3/1990 | Reed et al. | |
| 4,919,654 A | 4/1990 | Kalt | |
| 4,941,882 A | 7/1990 | Ward et al. | |
| 4,953,565 A | 9/1990 | Tachibana et al. | |
| 4,969,880 A | 11/1990 | Zamierowski | |
| 4,985,019 A | 1/1991 | Michelson | |
| 5,037,397 A | 8/1991 | Kalt et al. | |
| 5,086,170 A | 2/1992 | Luheshi et al. | |
| 5,092,858 A | 3/1992 | Benson et al. | |
| 5,100,396 A | 3/1992 | Zamierowski | |
| 5,134,994 A | 8/1992 | Say | |
| 5,149,331 A | 9/1992 | Ferdman et al. | |
| 5,167,613 A | 12/1992 | Karami et al. | |
| 5,176,663 A | 1/1993 | Svedman et al. | |
| 5,215,522 A | 6/1993 | Page et al. | |
| 5,232,453 A | 8/1993 | Plass et al. | |
| 5,261,893 A | 11/1993 | Zamierowski | |
| 5,278,100 A | 1/1994 | Doan et al. | |
| 5,279,550 A | 1/1994 | Habib et al. | |
| 5,298,015 A | 3/1994 | Komatsuzaki et al. | |
| 5,342,376 A | 8/1994 | Ruff | |
| 5,344,415 A | 9/1994 | DeBusk et al. | |
| 5,358,494 A | 10/1994 | Svedman | |
| 5,437,622 A | 8/1995 | Carion | |
| 5,437,651 A | 8/1995 | Todd et al. | |
| 5,527,293 A | 6/1996 | Zamierowski | |
| 5,549,584 A | 8/1996 | Gross | |
| 5,556,375 A | 9/1996 | Ewall | |
| 5,607,388 A | 3/1997 | Ewall | |
| 5,635,196 A | 6/1997 | Murphy | |
| 5,636,643 A | 6/1997 | Argenta et al. | |
| 5,645,081 A | 7/1997 | Argenta et al. | |
| 6,071,267 A | 6/2000 | Zamierowski | |
| 6,135,116 A | 10/2000 | Vogel et al. | |
| 6,241,747 B1 | 6/2001 | Ruff | |
| 6,287,316 B1 | 9/2001 | Agarwal et al. | |
| 6,345,623 B1 | 2/2002 | Heaton et al. | |
| 6,488,643 B1 | 12/2002 | Tumey et al. | |
| 6,493,568 B1 | 12/2002 | Bell et al. | |
| 6,553,998 B2 | 4/2003 | Heaton et al. | |
| 6,814,079 B2 | 11/2004 | Heaton et al. | |
| 8,216,198 B2 | 7/2012 | Heagle et al. | |
| 9,061,095 B2 * | 6/2015 | Adie | A61F 13/00068 |
| 2002/0077661 A1 | 6/2002 | Saadat | |
| 2002/0115951 A1 | 8/2002 | Norstrem et al. | |
| 2002/0120185 A1 | 8/2002 | Johnson | |
| 2002/0143286 A1 | 10/2002 | Tumey | |
| 2003/0120231 A1 | 6/2003 | Wang et al. | |
| 2003/0205318 A1 | 11/2003 | Ko et al. | |
| 2008/0032014 A1 * | 2/2008 | Frenz | B41M 3/006 |
| | | | 106/31.13 |
| 2010/0286638 A1 * | 11/2010 | Malhi | A61M 1/984 |
| | | | 604/313 |
| 2012/0024722 A1 * | 2/2012 | Chen | H01L 23/26 |
| | | | 206/204 |
| 2012/0061261 A1 * | 3/2012 | Hsu | B01D 53/261 |
| | | | 206/459.1 |
| 2013/0066301 A1 | 3/2013 | Locke et al. | |
| 2018/0264721 A1 * | 9/2018 | Iida | B29B 9/16 |
| 2019/0001030 A1 * | 1/2019 | Braga | A61M 1/60 |

FOREIGN PATENT DOCUMENTS

| | | |
|---|---|---|
| AU | 755496 B2 | 12/2002 |
| CA | 2005436 A1 | 6/1990 |
| CN | 105920687 B | 5/2018 |
| DE | 26 40 413 A1 | 3/1978 |
| DE | 43 06 478 A1 | 9/1994 |
| DE | 29 504 378 U1 | 9/1995 |
| DE | 10 2010 060 543 A1 | 4/2012 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 A1 | 7/2000 |
| GB | 692578 A | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 329 127 A | 3/1999 |
| GB | 2 333 965 A | 8/1999 |
| JP | 4129536 B2 | 8/2008 |
| SG | 71559 | 4/2002 |
| WO | 80/02182 A1 | 10/1980 |
| WO | 87/04626 A1 | 8/1987 |
| WO | 90/010424 A1 | 9/1990 |
| WO | 93/009727 A1 | 5/1993 |
| WO | 94/020041 A1 | 9/1994 |

(56) References Cited

FOREIGN PATENT DOCUMENTS

| WO | 96/05873 A1 | 2/1996 |
| WO | 97/18007 A1 | 5/1997 |
| WO | 99/13793 A1 | 3/1999 |

OTHER PUBLICATIONS

Susan Mendez-Eatmen, RN; "When wounds Won't Heal" RN Jan. 1998, vol. 61 (1); Medical Economics Company, Inc., Montvale, NJ, USA; pp. 20-24.
James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.
John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.
S.E. Greer, et al. "The Use of Subatmospheric Pressure Dressing Therapy to Close Lymphocutaneous Fistulas of the Groin" British Journal of Plastic Surgery (2000), 53, pp. 484-487.
George V. Letsou, MD., et al.; "Stimulation of Adenylate Cyclase Activity in Cultured Endothelial Cells Subjected to Cyclic Stretch"; Journal of Cardiovascular Surgery, 31, 1990, pp. 634-639.
Orringer, Jay, et al.; "Management of Wounds in Patients with Complex Enterocutaneous Fistulas"; Surgery, Gynecology & Obstetrics, Jul. 1987, vol. 165, pp. 79-80.
International Search Report for PCT International Application PCT/GB95/01983; dated Nov. 23, 1995.
PCT International Search Report for PCT International Application PCT/GB98/02713; dated Jan. 8, 1999.
PCT Written Opinion; PCT International Application PCT/GB98/02713; dated Jun. 8, 1999.
PCT International Examination and Search Report, PCT International Application PCT/GB96/02802; dated Jan. 15, 1998 & Apr. 29, 1997.
PCT Written Opinion, PCT International Application PCT/GB96/02802; dated Sep. 3, 1997.
Dattilo, Philip P., Jr., et al.; "Medical Textiles: Application of an Absorbable Barbed Bi-directional Surgical Suture"; Journal of Textile and Apparel, Technology and Management, vol. 2, Issue 2, Spring 2002, pp. 1-5.
Kostyuchenok, B.M., et al.; "Vacuum Treatment in the Surgical Management of Purulent Wounds"; Vestnik Khirurgi, Sep. 1986, pp. 18-21 and 6 page English translation thereof.
Davydov, Yu. A., et al; "Vacuum Therapy in the Treatment of Purulent Lactation Mastitis"; Vestnik Khirurgi, May 14, 1986, pp. 66-70, and 9 page English translation thereof.
Yusupov. Yu.N., et al; "Active Wound Drainage", Vestnki Khirurgi, vol. 138, Issue 4, 1987, and 7 page English translation thereof.
Davydov, Yu.A., et al; "Bacteriological and Cytological Assessment of Vacuum Therapy for Purulent Wounds"; Vestnik Khirugi, Oct. 1988, pp. 48-52, and 8 page English translation thereof.
Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.
Chariker, Mark E., M.D., et al; "Effective Management of incisional and cutaneous fistulae with closed suction wound drainage"; Contemporary Surgery, vol. 34, Jun. 1989, pp. 59-63.
Egnell Minor, Instruction Book, First Edition, 300 7502, Feb. 1975, pp. 24.
Egnell Minor: Addition to the Users Manual Concerning Overflow Protection—Concerns all Egnell Pumps, Feb. 3, 1983, pp. 2.
Svedman, P.: "Irrigation Treatment of Leg Ulcers", The Lancet, Sep. 3, 1983, pp. 532-534.
Chinn, Steven D. et al.: "Closed Wound Suction Drainage", The Journal of Foot Surgery, vol. 24, No. 1, 1985, pp. 76-81.
Arnljots, Bjom et al.: "Irrigation Treatment in Split-Thickness Skin Grafting of Intractable Leg Ulcers", Scand J. Plast Reconstr. Surg., No. 19, 1985, pp. 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.
Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.
N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (copy and certified translation).
K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.
G. Živadinovi?, V. ?uki?, Ž. Maksimovi?, ?. Radak, and p. Peška, "Vacuum Therapy in the Treatment of Peripheral Blood Vessels," Timok Medical Journal 11 (1986), pp. 161-164 (copy and certified translation).
F.E. Johnson, "An Improved Technique for Skin Graft Placement Using a Suction Drain," Surgery, Gynecology, and Obstetrics 159 (1984), pp. 584-585.
A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (copy and certified translation).
M. Schein, R. Saadia, J.R. Jamieson, and G.A.G. Decker, "The 'Sandwich Technique' in the Management of the Open Abdomen," British Journal of Surgery 73 (1986), pp. 369-370.
D.E. Tribble, An Improved Sump Drain-Irrigation Device of Simple Construction, Archives of Surgery 105 (1972) pp. 511-513.
M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).
C.E. Tennants, "The Use of Hypermia in the Postoperative Treatment of Lesions of the Extremities and Thorax,"Journal of the American Medical Association 64 (1915), pp. 1548-1549.
Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.
V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").
V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").
V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").
V.A.C. @ Therapy Clinical Guidelines: A Reference Source for Clinicians; Jul. 2007.
International Search Report and Written Opinion on International Patent Application No. PCT/US2020/016558 dated May 7, 2020 (10 pages).

\* cited by examiner

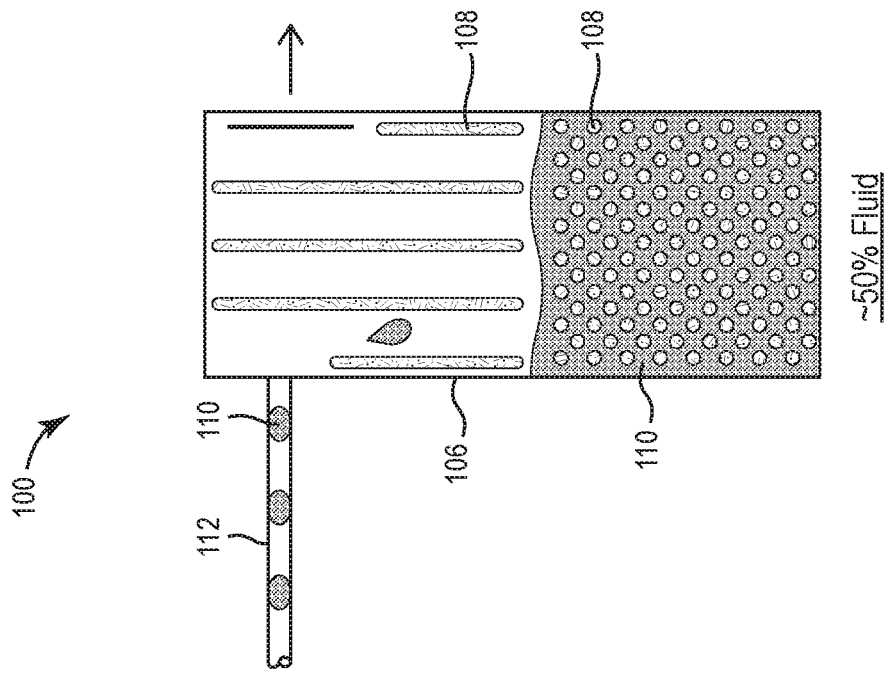
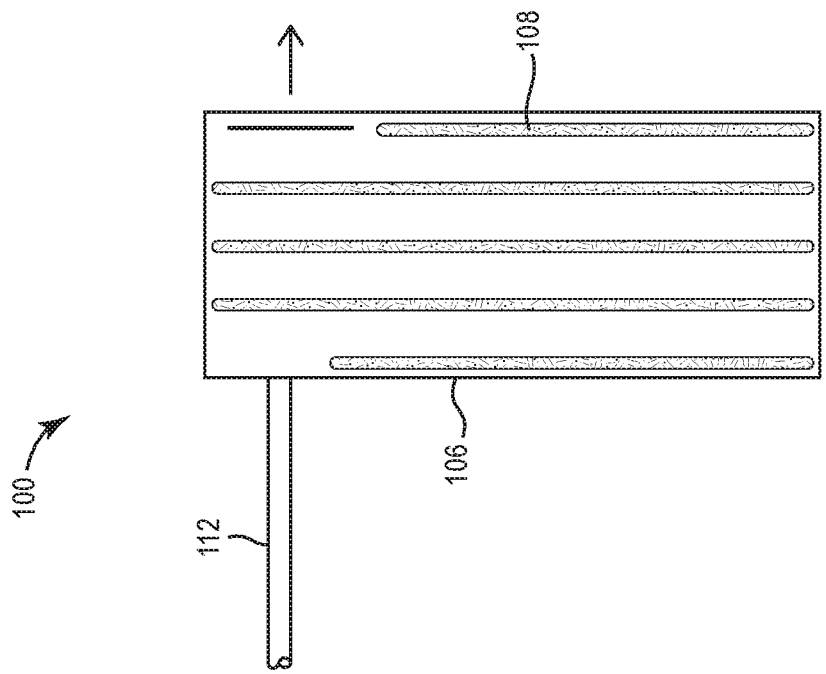

PRINTED ABSORBENT FOR USE IN WOUND FLUID COLLECTION CANISTERS

CROSS-REFERENCE TO RELATED APPLICATIONS

This application is a US national phase application under 35 USC § 371 of International Application No. PCT/US2020/016558 filed on Feb. 4, 2020, which claims the benefit of priority to U.S. Provisional Application No. 62/803,031, entitled "PRINTED ABSORBENT FOR USE IN WOUND FLUID COLLECTION CANISTERS" filed on Feb. 8, 2019, which are both hereby incorporated herein by reference in their entireties.

BACKGROUND

The present disclosure relates generally to a wound fluid collection canister to be used as part of a wound therapy system. The present disclosure relates more particularly to a printed absorbent in the form of superabsorbent projections for use in the wound fluid collection canisters.

Negative pressure wound therapy (NPWT) is a type of wound therapy that involves applying negative pressure (relative to atmospheric pressure) to a wound site to promote wound healing. Some NPWT systems include a pump which operates to maintain the wound site at negative pressure by removing wound exudate from the wound site. The wound exudate is typically routed to a canister or other container fluidly connected to the pump where the wound exudate is stored until emptied by a user. The canisters may contain an absorbent or solidifier for the purpose of stabilizing the collected wound fluids. In some cases, this may include superabsorbent polymer granules contained within a water dissoluble or cellulose pouch or a gelling agent which causes the collected would exudate to become gel-like in order to prevent sloshing in the canister. However, it is very easy for the pouches to be breached prior to use, which may result in the granules leaking from the pouches. The leaked granules may then cause blockages in various areas of the canister, such as in the conduits, filter chambers, or the collection tubing, which hinders the canisters ability to properly collect wound exudate and other fluids. Additionally, canisters may sometimes be dropped or otherwise damaged, which may also result in the pouches bursting or fracturing. It is therefore desirable to provide a highly robust and stabilized mechanism of absorbing fluid within the canister.

SUMMARY

One implementation of the present disclosure is a canister for a wound therapy device. The wound therapy device includes a canister body and a plurality of superabsorbent projections. The canister body is configured to contain wound exudate collected from a wound side. The plurality of superabsorbent projections are fixed to and extend from at least a portion of an interior surface of the canister, and may be formed in a plurality of shapes or patterns comprising circles, squares, hoops/halos, a range of lines, or any combination of said shapes.

Another implementation of the present disclosure is a method of making a canister for fluid collection. The method includes providing a canister body configured to contain wound exudate collected from a wound site. The method further includes preparing a slurry comprising a superabsorbent material. The method further includes applying the slurry onto an interior surface of the canister body in the form of a plurality of superabsorbent projections (nodules, dots, bumps, lumps, islands, protuberances), which may be formed in a plurality of shapes or patterns comprising circles, squares, hoops/halos, a range of lines, or any combination of said shapes.

Those skilled in the art will appreciate that the summary is illustrative only and is not intended to be in any way limiting. Other aspects, inventive features, and advantages of the devices and/or processes described herein, as defined solely by the claims, will become apparent in the detailed description set forth herein and taken in conjunction with the accompanying drawings.

BRIEF DESCRIPTION OF THE DRAWINGS

FIGS. 4A-4B are a cross-sectional view of the canister of FIG. 1 in use with a wound therapy system and shown collecting would exudate, according to an exemplary embodiment.

DETAILED DESCRIPTION

Overview

Referring generally to FIGS. 1-5, a printed absorbent for a wound fluid collection canister is shown, according to exemplary embodiments. In some embodiments, the canister may be configured for use with a wound therapy system, and components thereof are shown according to various exemplary embodiments. The printed absorbent of the exemplary embodiments includes a plurality of superabsorbent projections, which are fixed to and extending from the interior surface of the canister. In some embodiments, the superabsorbent projections may be printed onto a base of the interior of the canister, while in other embodiments, the superabsorbent projections may be printed over the entire interior surface of the canister. In some embodiments, the superabsorbent projections may be configured to swell and dissociate from the interior surface of the canister upon absorption of would exudate or other fluids.

Advantageously, the superabsorbent projections of the printed absorbent of the canister helps to ensure omnidirectional stabilization of fluids within the canister, wherein the canister may be of a variety of different shapes and sizes. In some embodiments, the superabsorbent projections may comprise a plurality of nodules, dots, bumps, lumps, islands, and protuberances extending from the interior surface of the canister. The superabsorbent projections are highly absorptive, and act to absorb wound exudate collected in the canister to prevent the sloshing and spillage of wound exudate from the canister when the canister is moved. Additionally, the superabsorbent projections are configured to remain intact while dissociating from the canister wall such that individual granules are not released into the canister which eliminates the risk of blockages within the canister and potential device failure.

Another advantage provided by the present invention is the increased optimization and customization of the design of the canister. The superabsorbent projections may be printed or otherwise adhered to a variety of locations within the canister, allowing for the customization of where wound exudate will be collected within the canister. Additionally, the methods described herein may be performed on a wide variety of shapes and sizes of canisters, such that the ideal canister may be determined based on factors other than the absorption of wound exudate. Additionally, the present invention provides a low cost solution to the absorption of wound exudate.

Canister with Printed Absorbent

Figure 1:
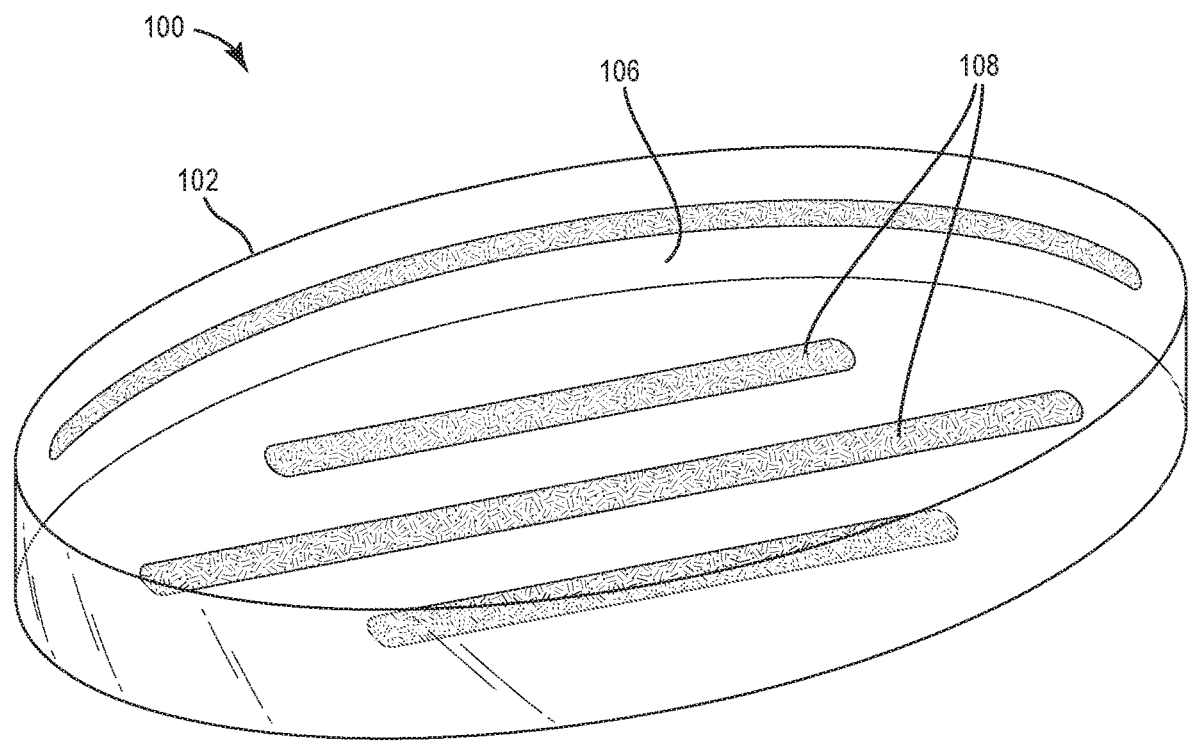
FIG. 1 is a perspective view of part of a collection canister for wound exudate and other fluids, to be used with a wound therapy system, according to an exemplary embodiment.
Figure 2:
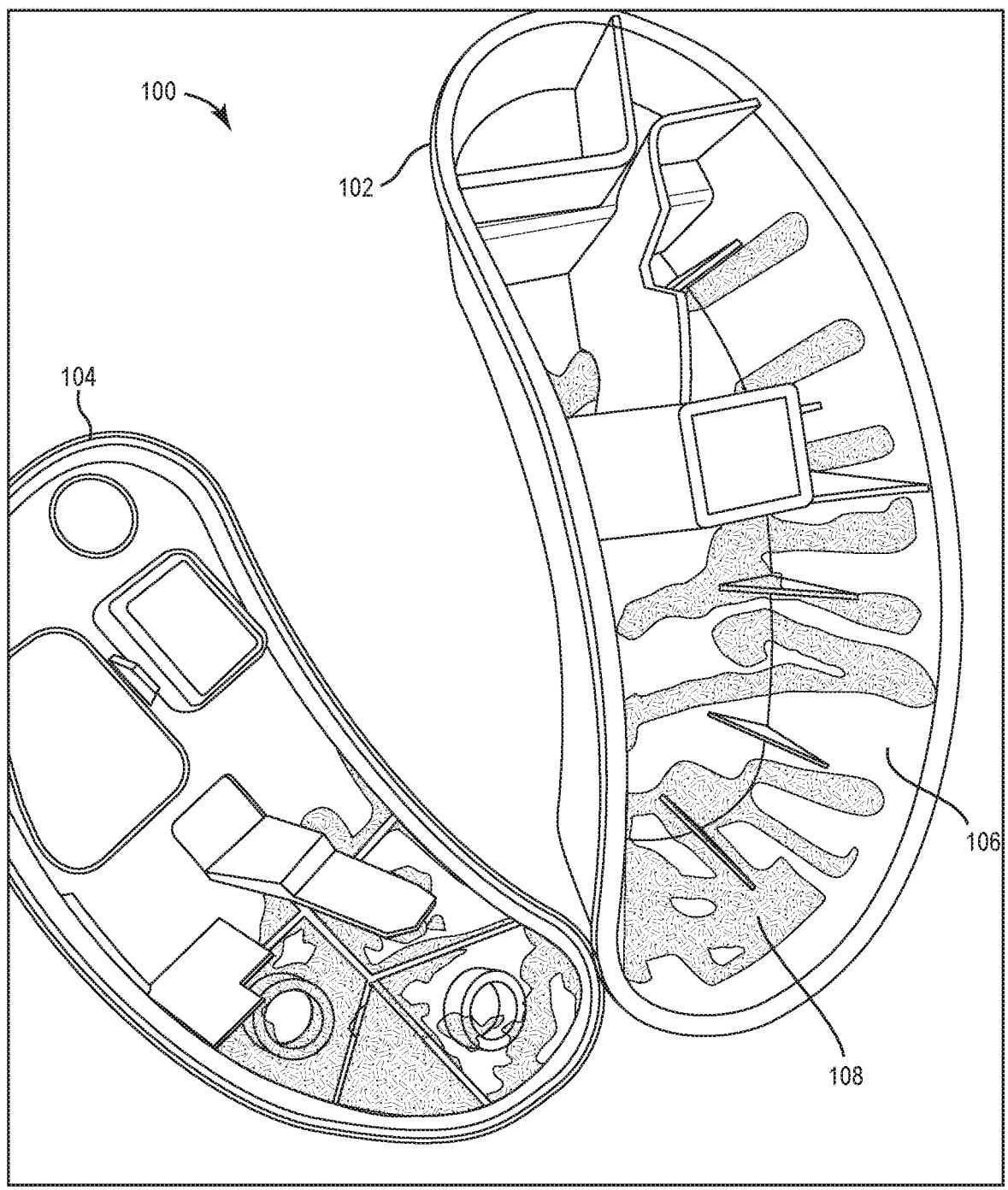
FIG. 2 is a cross-sectional view of the canister of FIG. 1, showing the superabsorbent projections and features of the canister prior to fluid collection, according to an exemplary embodiment.
Figure 3:
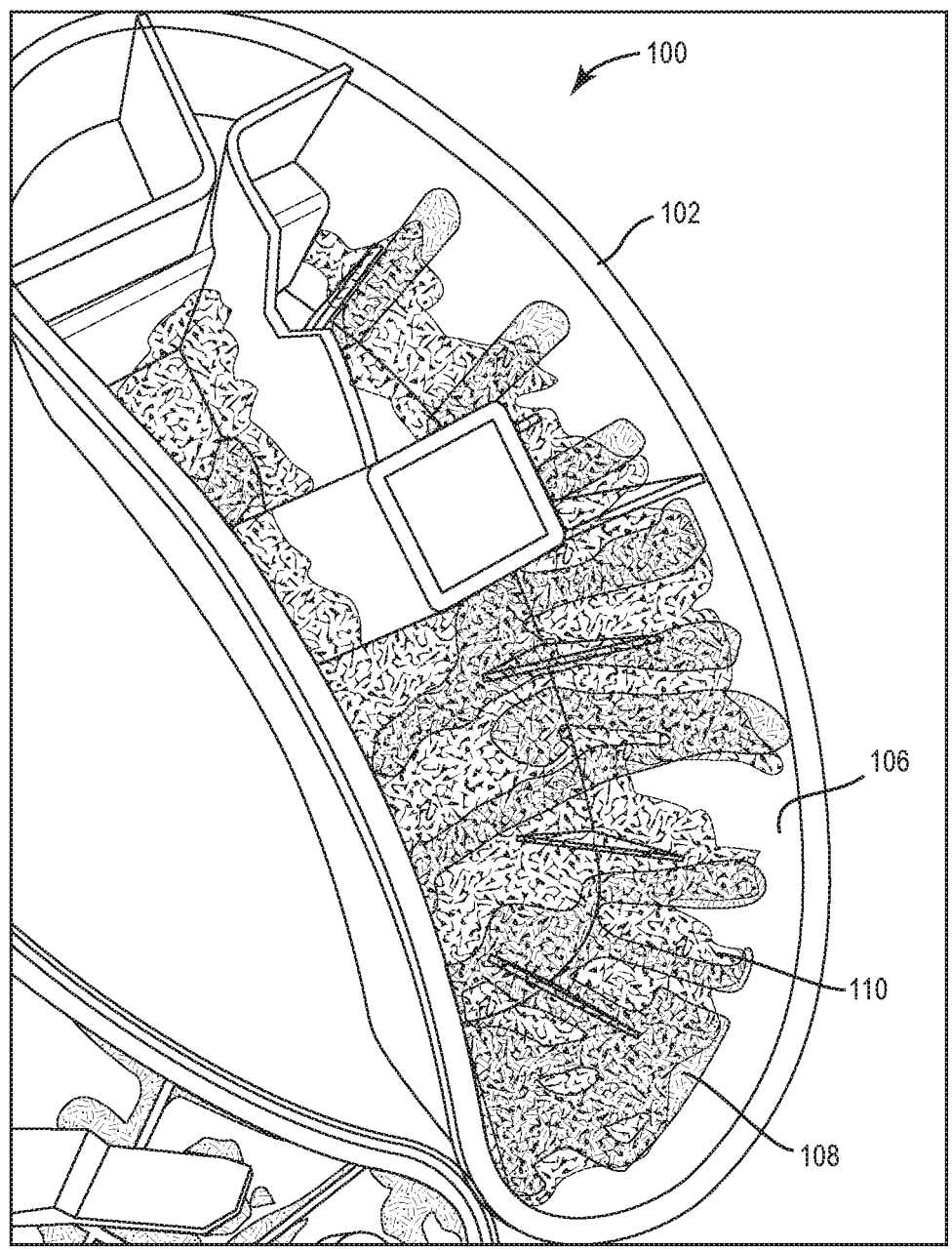
FIG. 3 is a cross-sectional view of the canister of FIG. 1, showing the superabsorbent projections and features of the canister after swelling due to fluid collection, according to an exemplary embodiment.
Figure 5:
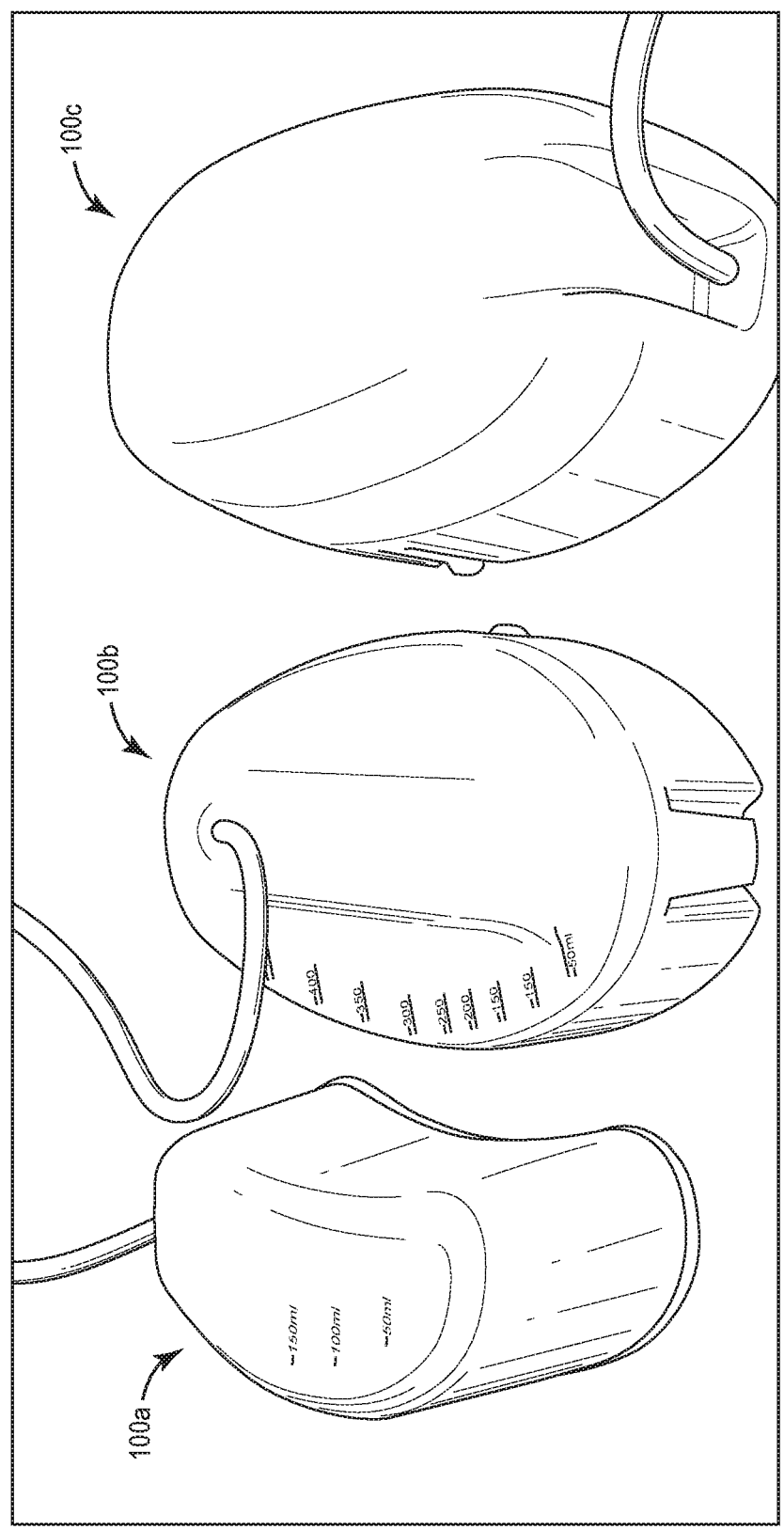
FIG. 5 is a perspective view of a plurality of collection canisters which may contain superabsorbent projections, according to an exemplary embodiment.

Referring now to FIGS. 1-5, a canister 100 including a printed absorbent is shown, according to various exemplary embodiments. In a brief overview, FIG. 1 is a perspective view of a first half of the canister 100, shown with lines of printed absorbent on the interior of the canister 100. FIG. 2 is a cross-sectional view of the canister 100, shown in two halves, prior to absorption of any wound exudate. FIG. 3 is a closer up cross-sectional view of the canister 100 shown with swollen printed absorbent, indicating the absorption of would exudate within the canister 100. FIGS. 4A-4B illustrate a cross-sectional view of the canister 100 in use with a wound therapy system. FIG. 5 is a perspective view of a plurality of collection canisters which may contain printed absorbent in the form of superabsorbent projections.

Canister 100 is shown generally to include a first half 102, a second half 104, an interior surface 106 and a plurality of superabsorbent projections 108 extending from an interior surface 106. In some embodiments, superabsorbent projections 108 may extend from the interior surface 106 on both the first half 102 and the second half 104 of canister 100. In other embodiments, superabsorbent projections 108 may extend from the interior surface 106 on one of the first half 102 and the second half 104 of canister 100. In some embodiments, superabsorbent projections 108 may extend from the interior surface 106 primarily near a base of the canister 100, where fluid will drop under gravity. In other embodiments, superabsorbent projections 108 may extend over a majority or the entire interior surface 106, such that the entire inside of the canister 100 is a mobile and omni-directional therapy unit configured to collect fluid in any location on the interior surface 106 of the canister 100. In some embodiments, the interior surface 106 of canister 100 may be molded with a plurality of grooves, in a shape and direction that does not hinder demolding, in order to help retain the printed adhesive and further to increase the relative amount of coating of printed adhesive and help with allowing fluid to access the printed absorbent in order for absorption.

In some embodiments, canister 100 may be used in combination with a therapy device. Therapy devices (not shown) can be configured to provide negative pressure wound therapy by reducing the pressure at a wound. Therapy devices can draw a vacuum at the wound (relative to atmospheric pressure) by removing fluids such as wound exudate. Wound exudate may include fluid that filters from a patient's circulatory system into lesions or areas of inflammation. For example, wound exudate may include water and dissolved solutes such as blood, plasma proteins, white blood cells, platelets, and red blood cells. Other fluids removed from the wound may include instillation fluid previously delivered to the wound. In other embodiments, canister 100 may be used independently of a therapy device, and may collect wound exudate without the use of a negative pressure system.

In various embodiments, collection canister 100 can be formed in a variety of shapes, sizes, and of various materials for the collection of wound exudate. In the embodiment shown in FIG. 5, a plurality of canisters 100a-100c are shown, according to an exemplary embodiment. In some embodiments, canister 100a has a size of 300 cm$^3$. In some embodiments, canister 100b has a size of 500 cm$^3$. In some embodiments, canister 100c has a size of 1000 cm$^3$. In still other embodiments, canister 100 may be larger than 1000 cm$^3$ or smaller than 300 cm$^3$.

Superabsorbent Projections

In some embodiments, canister 100 includes a plurality of superabsorbent projections 108 fixed to and extending from the interior surface 106 of canister 100. A top portion of superabsorbent projections 108 extend into an interior cavity of canister 100. In some embodiments, superabsorbent projections 108 comprise a plurality of nodules, dots, bumps, lumps, islands, and lines.

In some embodiments, superabsorbent projections 108 may be formed from or otherwise include a superabsorbent polymer in the form of granules. The superabsorbent polymer may include Luquasorb 1160 or 1161, such as may be commercially available from BASF. The granules may be contained in a water soluble carrier polymer. One example of the water soluble carrier polymer is polyvinylpyrrolidone (PVP). The superabsorbent polymer of the superabsorbent projections 108 and the water soluble polymer may be formed into a slurry or a suspension using an organic solvent. The organic solvent may include propanone or propanol, and may aid in delivery of the superabsorbent projections 108 to the first side 114 of elastic foam layer 106. In some embodiments, to increase the softness of the superabsorbent granules, a plasticizer may be added to the slurry. In one embodiment, the plasticizer may be water. In some embodiments, the slurry to form the superabsorbent projections 108 may have a formulation of 20 parts by mass of PVP, 10 parts by mass of a superabsorbent polymer, 1 part by mass of glycerol, and 100 parts by mass of propanone. In some embodiments, to plasticize the granules, 1 part to 2 parts by mass of water may be added to the slurry mixture. In other embodiments, a water soluble polymer superabsorbent precursor, such as acrylic acid or 2-acrylamido-2-methyl-propanesulfonic acid (AMPS), with suitable UV curing additives, may replace the superabsorbent polymer. Such a precursor may be a relatively low viscosity solution and can be printed interior surface 106 of canister 100 and exposed to UV light to form a soft gel, eliminating the need for a plasticizer. In some embodiments, the water soluble polymer superabsorbent precursor may be similar to that used for preparing hydrogel coatings. In some embodiments, the superabsorbent polymer may be formed from a cross-linked water soluble polymer, based on poly acrylic acids and acrylamides, such as acrylamide and 2acrylamido2methylpropan sulfonic acid (AMPS). In other embodiments, an uncross-linked solution of these polymers may be coated onto the interior surface 106 of canister 100 and then cross linked after application, through a process such as exposure to UV or during the gamma sterilization process of the canister 100. The cross-linking of the polymers after application to the interior surface 106 would allow for clear superabsorbent projections 108, which may permit the level of fluid within superabsorbent projections 108 to be easily observed.

The slurry mixture is applied to interior surface 106 of canister 100 to form superabsorbent projections 108. In some embodiments, the process of applying the slurry mixture to interior surface 106 of the canister 100 may occur prior to the assembly and welding of the canister 100, such that the slurry mixture is applied to both the first half 102 and second half 104 of canister 100 before they are sealed together. In some embodiments, the slurry may be applied to interior surface 106 through standard printing methods, such as silk screen printing, gravure printing, or by x-y plotter printing. In the embodiment shown, the slurry mixture may be applied to both the first half 102 and the second half 104 of canister 100 prior to welding and sealing of canister 100. In other embodiments, canister 100 may comprise a removable lid, such that the slurry mixture may be applied through an opening near the top of the canister 100. In still other embodiments, canister 100 may comprise an opening, such as an opening of which tubing 112 may be inserted into, such that the slurry mixture may be applied through the opening on a side of the canister 100. Superabsorbent projections 108 may be in any non-contiguous shapes such as circles, squares, hexagons, hoops/halos, stars, crosses, a range of lines, or any combination of shapes. Superabsorbent projections 108 may be printed such that they are substantially evenly distributed on the interior surface 106. In other embodiments, superabsorbent projections 108 may be printed in an uneven (e.g. non-uniform, random, etc.) pattern on interior surface 106. In some embodiments, superabsorbent projections 108 are arranged in a non-contiguous manner (i.e. isolated, separated, spaced-apart, non-touching, etc.) so that a region remains between superabsorbent projections 108. In other embodiments, superabsorbent projections 108 may be printed contiguously around various areas of interior surface 106 of the canister 100. In some embodiments, superabsorbent projections 108 may include a flexible plasticized hydrophilic polymer matrix having a substantially continuous structure.

In some embodiments, the slurry mixture may be applied to interior surface 106 in a pattern and particular location within the canister 100 such that the superabsorbent projections 108 will be positioned over the areas in which fluids will collect in the canister. In some embodiments, the slurry mixture is applied to a base of the canister 100, as fluid will collect in the base of the canister 100 due to gravity. In other embodiments, the slurry mixture may be applied over a majority or the entire interior surface 106, such that the entire inside of the canister 100 is a mobile and omni-directional therapy unit configured to collect fluid in any location on the interior surface 106 of the canister 100. In some embodiments, the slurry mixture may be applied in a coating to cover certain areas of the canister 100 to a degree, such as the areas of the canister 100 which have small indentations and nooks.

In some embodiments, in order to aid adhesion of the superabsorbent projections 108 to interior surface 106, interior surface 106 may have a round surface finish, such as a Standex finish, in order to facilitate keying of the two materials to ensure adhesion. In some embodiments, this finish may be incorporated into canister 100 during the injection molding process used to form canister 100, while in other embodiments, the finish may be imparted throughout the canister 100 using a local shot-blasting after injection molding. In still further embodiments, the interior surface 106 of canister 100 may be plasma treated or have a solvent applied in the areas where superabsorbent projections 108 will be applied to aid in bonding with superabsorbent projections 108. In some embodiments, the slurry mixture may further include a fluid-reactive dye (such as a blue dye) that is included into the superabsorbent projections 108. The dye used in superabsorbent projections 108 may act to disguise the collected wound exudate 108, while still allowing for a visual indication as to the level of fluid which has been collected by the superabsorbent projections 108.

Prior to application of the slurry mixture to the interior surface 106, the interior surface 106 may be printed with an adhesive coated film in the areas to which superabsorbent projections 108 may be applied. In some embodiments, the adhesive applied to interior surface 106 is moisture vapor transmitting and/or patterned to allow passage of water vapor therethrough. The adhesive may include a continuous moisture vapor transmitting, pressure-sensitive adhesive layer (e.g., a polyurethane or polyethylene-based pressure sensitive adhesive). In some embodiments, the adhesive may comprise a water soluble/sensitive adhesive. In some embodiments, the adhesive may include one of a viscose, gel-like UV-curing, cyanoacrylate, polyacrylate, or other structural and gap-filling adhesive. In other embodiments, the adhesive may include a polyvinyl alcohol (PVOH) and a copolymer with polyvinyl acetate PVAc). In some embodiments, the PVAc copolymers may provide a higher degree of bonding to the canister 100. The adhesive may be applied in a pattern which reflects the optimum locations for absorbent deposition. In some embodiments, the ratio of PVOH (PVAc, hydrolysis, and molecular mass) may be used to control the water sensitivity of the adhesive and adjust the release rate of the superabsorbent projections 108 from the interior surface 106. Prior to curing but after the application of the adhesive, the canister is exposed to the superabsorbent polymer in the form of granules, which are adhered to the adhesive. Following the adherence of the granules to the adhesive on the interior of canister 106, the canister 100 may be cured. In some embodiments, if each granule of the superabsorbent polymer is bound to the adhesive on the interior surface 106, it will allow for the de-bonding of the superabsorbent projections 108 once they have absorbed wound exudate and other fluids.

Superabsorbent projections 108, as shown in FIGS. 3 and 4A-4B are configured to swell upon absorption of fluid 110. As shown in FIGS. 4A-4B, fluid 110 may enter the canister 100 via tubing 112. In some embodiments, tubing 112 may be part of a therapy device. Fluid 110 may, for example, be wound exudate fluid from a wound. Superabsorbent projections 108 may be highly hydrophilic, such that they attract and absorb fluid 110 within the canister 100. Each of the superabsorbent projections 108 may absorb and swell upon absorption of fluid 118, providing a visual indication of which portion of canister 100 has absorbed fluid. In some embodiments, superabsorbent projections 108 may be configured to dissociate from the interior surface 106 upon absorption of fluid 110. The superabsorbent projections 108 should only dissociate from the interior surface 106 after absorption of fluid 110, and should not dissociate further into individual granules of the superabsorbent polymer. In some embodiments, the ratio of the slurry mixture when forming the superabsorbent projections 108 may be modified to control the degree of dissociate of the superabsorbent projections 108 from the interior surface 106. As shown in FIG. 4b, after dissociation of the superabsorbent projections 108 which have absorbed fluid 110, the absorbed fluid 110 may collect in certain areas of the canister 100 and provide a visual indication as to how much fluid 110 has been absorbed and how full canister 100 may be. In some embodiments, superabsorbent projections 108 are configured to prevent canister 100 from leaking any fluid, as fluid

CONFIGURATION OF EXEMPLARY EMBODIMENTS

The construction and arrangement of the systems and methods as shown in the various exemplary embodiments are illustrative only. Although only a few embodiments have been described in detail in this disclosure, many modifications are possible (e.g., variations in sizes, dimensions, structures, shapes and proportions of the various elements, values of parameters, mounting arrangements, use of materials, colors, orientations, etc.). For example, the position of elements can be reversed or otherwise varied and the nature or number of discrete elements or positions can be altered or varied. Accordingly, all such modifications are intended to be included within the scope of the present disclosure. The order or sequence of any process or method steps can be varied or re-sequenced according to alternative embodiments. Other substitutions, modifications, changes, and omissions can be made in the design, operating conditions and arrangement of the exemplary embodiments without departing from the scope of the present disclosure.

What is claimed is:

1. A canister for fluid collection, the canister comprising:
   a canister body configured to contain wound exudate collected from a wound site; and
   a plurality of superabsorbent projections fixed to and extending from at least a portion of an interior surface of the canister body, wherein the superabsorbent projections comprise a polymer in the form of granules and are configured to dissociate from the interior surface of the canister body while remaining intact such that the superabsorbent projections do not break down to individual granules, wherein the superabsorbent projections comprise a flexible plasticized hydrophilic polymer matrix having a substantially continuous internal structure.

2. The canister of claim 1, wherein the superabsorbent projections are configured to swell upon absorbing the wound exudate and dissociate from the interior surface of the canister body.

3. The canister of claim 1, wherein the interior surface of the canister comprises a rough surface finish to aid in adhering of the superabsorbent projections to the interior surface.

4. The canister of claim 1, wherein the superabsorbent projections are non-contiguous.

5. The canister of claim 1, wherein the superabsorbent projections are printed onto the interior surface of the canister by screen printing, gravure printing, or by x-y plotter printing.

6. The canister of claim 1, wherein the granules are contained in a water soluble carrier polymer.

7. The canister of claim 1, wherein the interior surface is coated with an adhesive film prior to application of the superabsorbent projections.

8. The canister of claim 7, wherein the adhesive film comprises one of a viscose, cyanoacrylate, polyacrylate, gel-like UV-curing, or polyvinyl alcohol.

9. The canister of claim 1, wherein the superabsorbent projections are distributed in a non-uniform pattern on the interior surface of the canister body.

10. A method of making a canister for fluid collection comprising:
    providing a canister body configured to contain wound exudate collected from a wound site;
    preparing a slurry comprising a superabsorbent material, wherein the slurry comprises a polymer in the form of granules; and
    applying the slurry onto an interior surface of the canister body in the form of a plurality of superabsorbent projections, wherein the superabsorbent projections are configured to dissociate from the interior surface of the canister body while remaining intact such that the superabsorbent projections do not break down to individual granules, wherein the superabsorbent projections comprise a flexible plasticized hydrophilic polymer matrix having a substantially continuous internal structure.

11. The method of claim 10, wherein the plurality of superabsorbent projections are operable to absorb would exudate collected in the canister.

12. The method of claim 11, wherein the superabsorbent projections are configured to swell and dissociate from the interior surface of the canister body upon absorbing the wound exudate.

13. The method of claim 10, further comprising applying a rough surface finish to the interior surface of the canister to aid in adhering of the superabsorbent projections to the interior surface.

14. The method of claim 10, wherein the granules are contained in a water soluble carrier polymer.

15. The method of claim 10, wherein the interior surface is coated with an adhesive film prior to application of the superabsorbent projections, and the adhesive film comprises one of a viscose, cyanoacrylate, polyacrylate, gel-like UV-curing, or polyvinyl alcohol.

* * * * *